United States Patent [19]

Duinker

[11] 4,146,794
[45] Mar. 27, 1979

[54] TOMOMETRY SYSTEM HAVING PROVISIONS FOR SELECTIVELY ADJUSTING THE FORMAT OF A DISPLAYED PICTURE

[75] Inventor: Simon Duinker, Bloemendaal, Netherlands

[73] Assignee: "De Oude Delft" N.V. Optische Industrie, Netherlands

[21] Appl. No.: 840,130

[22] Filed: Oct. 7, 1977

[30] Foreign Application Priority Data

Oct. 15, 1976 [NL] Netherlands ........................ 7611420

[51] Int. Cl.$^2$ ........................ A61B 6/02; H04N 5/32
[52] U.S. Cl. ........................ 250/445 T; 250/416 TV; 358/111
[58] Field of Search .................... 250/445 T, 416 TV; 358/111

[56] References Cited

U.S. PATENT DOCUMENTS 4,017,679   4/1977   Kemner et al. ...................... 358/111

Primary Examiner—Alfred E. Smith
Assistant Examiner—T. N. Grigsby
Attorney, Agent, or Firm—O'Brien and Marks

[57] ABSTRACT

An apparatus for examining an object placed on a support arrangement and located between a source of penetrating radiation and a radiation responsive detector arrangement comprising an image intensifier tube in conjunction with an internal or external continuous detector screen, the combination of said source and said detector arrangement together with adjustable beam collimating means being mounted so as to allow for a rotation relative to the object about an axis extending perpendicularly to a cross-sectional plane of said object, comprising an electronic control arrangement for selectively adjusting the format and/or resolution of a television pattern obtained by scanning the image at the target of a television camera tube and resulting from the projection of the image produced at the output of said detector arrangement, and position selecting means for orientating the position of said support arrangement selectively and in dependence of the adjustment of said electronic control arrangement with respect to the position of said source, detector arrangement and collimating means in such a manner that said body can be irradiated with a substantially conical beam or with a substantially flat diverging beam.

4 Claims, 1 Drawing Figure

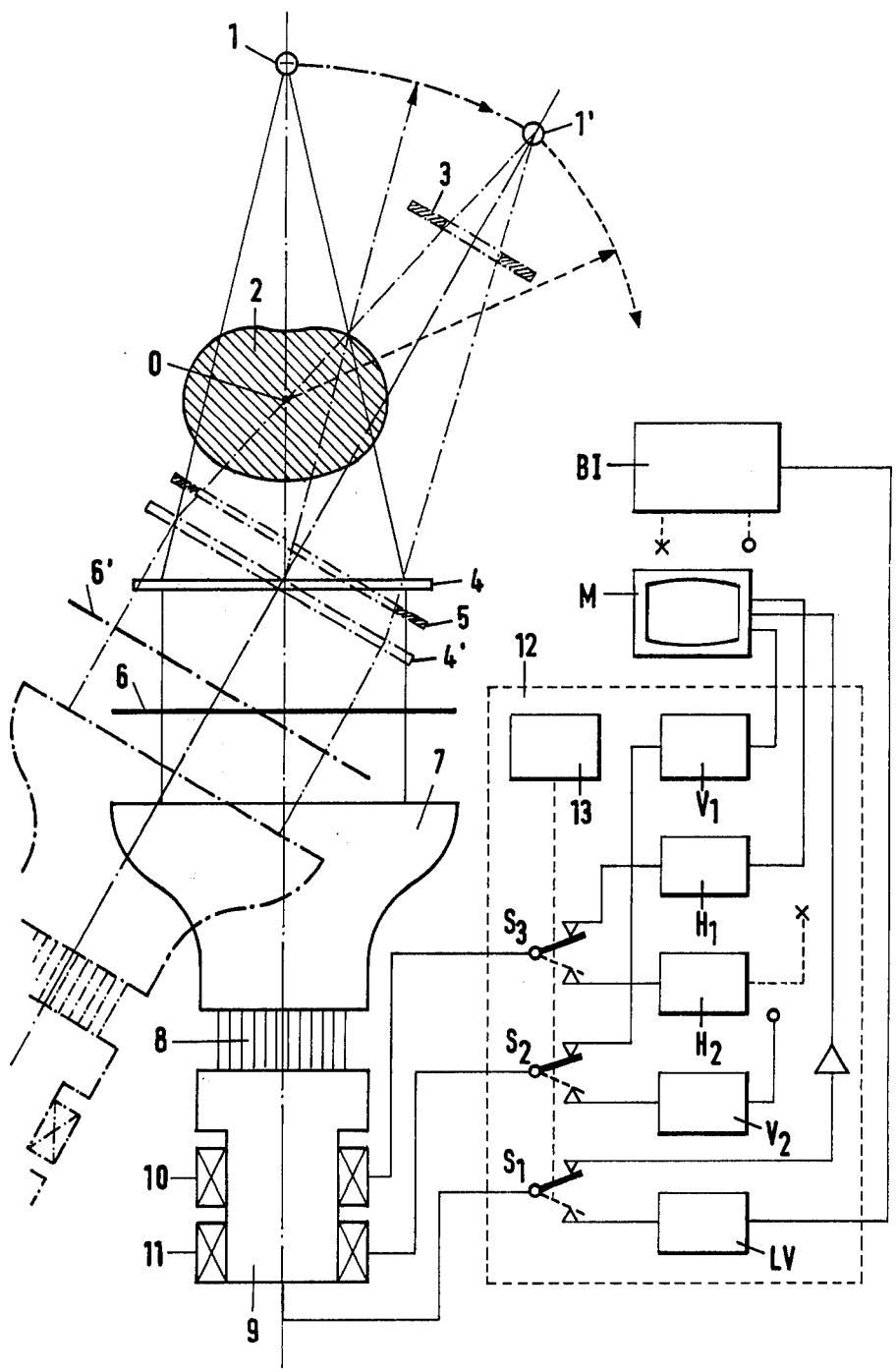

TOMOMETRY SYSTEM HAVING PROVISIONS FOR SELECTIVELY ADJUSTING THE FORMAT OF A DISPLAYED PICTURE

The invention relates to a tomometry system comprising a source for producing shortwave radiation, e.g. X-ray or gama-radiation, an object carrier, a set of slotted masks adapted for irradiation of an object carried by the object carrier by means of one or more fan-shaped beams of radiation, a detector for converting radiation transmitted across and along the object into electrical signals, and a picture reconstruction device for processing said electrical signals.

As conventional in tomometry, an object to be examined is irradiated by a substantially flat, diverging beam of shortwave radiation. To this effect there is positioned opposite the radiation source a mask having one or more parallel slots so that one or more disc-shaped sections of the object in question can be irradiated. On the capture screen of the detector device positioned opposite a thus irradiated object, there are projected one or more superimposed frames via a corresponding slotted mask, each of said frames corresponding to the transmission picture of a disc-shaped section of the object, as defined by the mask positioned at the source side. The detector device is adapted for deriving from each such frame an electrical signal, a so-called signal profile.

Dutch patent application No. 76.05253 describes such a tomometry system, wherein a picture produced on the capture screen of the detector device is imaged onto the input screen of an image intensifier. The output screen of said intensifier is directly coupled to the pickup side of a video camera. A frame formed at the pickup side of said video camera may be read out, e.g. line-wise, and by each time integrating the thus read out image lines column-wise, there is obtained an electric output signal, the so-called signal profile, of which the instantaneous value of each of its elements is a measure for the total transmission of an examined disc-shaped object section along a beam originating from a radiation source and incident at a given angle.

By irradiating the object successively from various angles, eventually a tomogram can be reconstructed by means of the picture reconstruction device utilising the various signal profiles obtained.

Such a reconstruction of a tomogram requires a specific time which is substantially determined by the time required for the irradiation of the object from all directions desired, and the time necessary for processing the signal profiles obtained through radiation to a form suitable for tomographic representation. In a system thus organised it cannot be determined until a complete tomogram had been obtained whether the respective object section actually contains the desired detailed information. A consequence thereof is that in practice it will frequently occur that the examined object section of which the complete tomogram has been made, is not the section optimal for the examination concerned, so that again successive tomograms have to be made at different heights until a cross-section of the object is found that is suitable for the examination in question.

Such a procedure wherein successively different tomograms have to be made has serious disadvantages. The major disadvantage is that the repeated tomograms to be made constitute an inadmissible physical strain on a patient to be examined, while the repeated exposure to a considerable radiation dose is very detrimental to the condition of the patient.

Since the conventional tomography systems do not offer possibilities to determine, prior to the making of a tomogram, where the optimal cross-sections(s) has (have) to be chosen, this would have to be determined by means of a separate device. To this effect use could be made of a normal X-ray installation which can produce an overall picture which allows the determination of the location of organs to be examined in cross-section, which location may e.g. be marked onto the patient, after which the tomography system can make the tomograms in accordance with said indications. Such an elaborate procedure is e.g. also conventional in the irradiation of organs by means of linear accelerators, wherein the location of the organ in question is accurately determined beforehand in a so-called simulator.

It is the object of the invention to provide an improvement of a tomography system of the above described type in the sense that the possibility is offered, prior to proceeding to making a tomogram, and without the necessity of using the above described elaborate procedure, to simply render the system suitable for obtaining an overall X-ray picture by means of which, prior to the making of the final tomogram, it is possible to accurately determine the proper location of the cross-sections of the object relevant to the examination in question, with the possibility of altering the system thereafter in a simple manner for tomograhic use.

The present invention is based on the insight that in a tomographic system of the type proposed in the above cited Dutch patent application No. 76.05253, the thickness of an object cross-section, the number of picture elements per section, as well as the position thereof, at least in so far these parameters play a role in the single profile formation, are exclusively determined by the manner in which the picture formed at the pickup side of the video camera is read out.

Starting from this insight a tomographic system according to the present invention is characterized in that one end the means serving for the deflection of the scanning beam of the video camera which, in an optical sense, is being coupled rigidly with the output of the detector arrangement, are coupled to a selectively switchable, electronic control device, by means of which the format and/or resolution of the picture as is being read out by the video camera can be adjusted to selected values, and on the other hand a selectively adjustable, positioning device is being provided for grouping spatially relative to one another, and dependent on the operating mode selected for said electronic control device, the combination of radiation source, slotted masks and detector device, with respect to the object carrier in such a way that either an overall picture of an object carried by the object carrier, or a tomographic image of one or more cross-sections of the object portion corresponding to said overall picture can be made. By means of said selectively adjustable positioning device it is possible to adjust the relative position of the object with respect to the radiation source and detector device assembly by vertical and lateral displacement in a required manner.

For obtaining a "total" or overall picture of the object in question, in other words a normal X-ray picture, when the object in question is irradiated for a given direction, it is necessary when switching over from one operating mode of the electronic control device to the other, to also ensure that the slotted masks mounted in front of the radiation source and of the capture screan of the detector device can be displaced such that the radiation source positioned just opposite the object can produce such an overall picture onto the capture screen of the detector device. When the electronic control device has been switched over in the said operating mode, a substantially rectangular picture format can be read out, whose area is substantially equal to the effective area of the input screen of the video camera tube.

The organisation of the above-mentioned switchable electronic control device is determined by the type of scanning chosen for the video camera tube. It is usual to select a horizontal scanning method; the number of scanning lines being chosen such that an optimal resolution is obtained.

When horizontal line scanning is being used, this will practically mean that a picture of 625 lines, each having a length corresponding to the effective width of the input screen of the video camera tube, is scanned. When said scanning takes place at a rate of 50 fields per second, this means a line frequency of 15625 Hz. By successively making the deflection signal serving for the vertical deflection effective over a selected number of image lines and from a selected point of time in the period, of such a deflection signal respectively, one or more picture formats, each having a selected image line number, can be scanned. If desired, the same picture format area can be scanned, with a smaller number of image lines, when a correspondingly reduced resolution of the scanned picture is deemed sufficient.

After such an overall picture or a normal X-ray picture of a specific part of an object has been rapidly and simply obtained, it will be possible to make a choice, on account of said overall picture, of the object cross-section or sections to be tomographically imaged, after which said position device is so adjusted that said slotted masks and the radiation source and capture screen of the detector device assembly may form a picture of the required object disc. During this procedure the electronic control device is adjusted to an operating mode through which a picture format having a height sufficient for forming the signal profiles can be scanned. Typically a picture frame as imaged on the input screen of the video camera tube, is scanned line-wise to this effect, with a number of image lines necessary for the required resolution.

The manner in which the above-mentioned adjustments have to be effected is determined by the type of organisation that is chosen for obtaining the tomogram. Various possibilities exist therefor.

According to the proposals laid down in Dutch application No. 76.05687, a tomogram is for instance obtained by irradiating the object in the indicated cross-section thereof by means of a fan-shaped beam which is confined at one side by the relative axis of rotation, while the outer ray at the other side is disposed beyond the object. If such an organisation is used, to which the invention is not limited as a matter of fact, said adjustment of the slotted masks and the radiation source and detector assembly should be such that besides the vertical adjustment corresponding to the determined location of the object cross-section, likewise such a spatial mutual regrouping of the radiation source, the object and the detector device takes place that one of two outer rays of the fan-shaped beam extends through the relative axis of rotation of the system.

However, the invention is not restricted to the above-mentioned line-wise scanning. For the reasons indicated in the Dutch patent application (vertical scanning) it may be advantageous to scan, for tomographic purposes, a picture formed on the input target of the video camera tube, according to paths extending transversely to the horizontal direction. In a detector device designed according to the proposals laid down in the above Dutch patent application, said electronic control device, in the situation wherein the above-mentioned general picture is desired, should be switched in such an operating mode that the signals for deflection, in a direction extending transversely to the horizontal direction, have an amplitude that is sufficient for covering the entire effective "height" of the image as projected onto the target of the video camera tube, the definition of the scanned picture being determined by the frequency at which said transversed direction is scanned. The electric signals produced at the output of the video camera tube, as a result of the scanning according to the above described fields, can be reproduced or recorded by means of known per se monitor or memory device.

Without limitation of the generality, one embodiment of the present invention will be explained by way of example, wherein use is made of organisations derived from proposals as laid down in the above-mentioned Dutch patent application No. 76.05687 and "vertical scanning", and with reference to the accompanying drawing. For simplicity's sake, said embodiment will be limited to obtaining only a single tomographic image.

The drawing shows a radiation source for producing a beam of short-wave radiation, e.g. X-ray radiation, indicated by 1. An object to be examined carried by an object carrier, not shown, is indicated by 2. A first movable slotted mask is indicated by 3, which slotted mask, as will be explained in the following, can be positioned selectively between the object 2 and the source 1, in or beyond the radiation beam produced by source 1. Between the object 2 and a capture screen 4 a second movable slotted mask 5 may be selectively disposed. It is observed that source 1, object 2 (object cross-section) the two slotted masks 3 and 5, and the capture screen 4 are shown in top view. A lens system 6 serves for projecting an image formed on the screen 4 as a result of irradiation of the object on the input side of a luminance amplifier 7. The output side of said amplifier is coupled directly, e.g. by fibre-optics arrangement 8, to the pickup side of a video camera tube 9. Said tube is provided with means 10 for deflecting an electron beam in horizontal or image line direction for scanning the image formed on the input screen, and with means 11 for vertically deflecting said scanning beam. These deflecting means 10 and 11, as well as the output of the camera tube 9, are connected to a switchable electronic control device indicated in general by 12. Said control device comprises an operating mode switch $S_1$, $S_2$, $S_3$ by means of which it is possible to selectively switch on an operating mode suitable for forming an overall picture, or an operating mode suitable for making a tomogram. When said mode switch has been switched into the position shown in the drawing, an overall picture may be formed on a monitor M known per se. In said operating mode the deflection means 10 are coupled to a generator $H_1$ for transmitting a horizontal deflection signal having a frequency of e.g. 15625 Hz. Said deflection signal is generally sawtooth-shaped and is likewise used for the horizontal deflection of the monitor. In said operating mode the means 11 serving for the vertical deflection are coupled to a generator $V_1$ for producing a vertical deflection signal at a frequency of e.g. 50 Hz.

This signal is likewise generally a sawtooth-shaped voltage which is also used for the vertical deflection of the monitor. The mode switch also affects a command unit 13 under control of which the above described locating device can group the radiation source, object carrier, slotted masks and detector device spatially relative to each other in accordance with the required operating mode. In the operating mode wherein an overall picture has to be formed, said command unit in the shown position of the mode switch S is conditioned in such a manner that source 1 is precisely opposite the object 2 as indicated by the drawn lines of the radiation beam, whereby the two slotted masks 3 and 5 are positioned and diaphragmed in accordance with the spatial angle defined for said beam. When switched into such operating mode, the output signal of the camera tube 9 is applied to a video amplifier, the output signal of which functions as luminance control for monitor M. Thus an overall picture can be formed of the object 2 by means of the above described arrangement.

As already explained in the foregoing, the appropriate position and height of the desired object cross-section(s) can be determined on the basis of such an overall picture; hereafter by setting the mode switch 5 from the position shown into the position indicated by broken lines, an operating mode is obtained wherein a tomogram can be made. In said operating mode the deflection means 10 are coupled to a horizontal deflection generator $H_2$ which produces a deflection signal of e.g. 625 Hz by means of which the scan beam of camera tube 9 is deflected. Said deflection signal is generally a sawtooth-shaped voltage. The vertical deflection means 11 are coupled to a vertical deflection generator $V_2$ thereby providing read out in a direction which is transversely oriented relative to the image line direction. As also indicated in the above-mentioned Dutch application, to that end advantageously use can be made of a square-shaped voltage having e.g. a frequency of 250 kHz. In this position of the mode switch S, the command unit 13 is also conditioned in such a manner that the two slotted masks 3 and 5 respectively are positioned between the source and the object and between the object and the capture screen 4 such that the radiation source when moved in lateral direction into the position 1' forms a picture on the screen 4 corresponding to a disc-shaped cross-section of said object. It is observed that in this situation the source 1, the two slotted masks 3 and 5, the screen 4, the lens system 6 and the image intensifier 7 form an assembly which in its entirety can rotate with respect to an axis of rotation 0 (perpendicularly to the plane of drawing) so as to perform a rotational movement about the object. Use is made in this situation of a so-called half beam, which means that during this rotational movement the beam is always limited on one side by the axis of rotation 0, while the outer ray on the other side lies outside the object. The required regrouping of the source, the slotted masks, the object carrier and the detector device may be effected under control of the command unit 13 in dependence on the position of the mode switch S. In the operating mode for making tomographic pictures, the output of video camera tube 9, via the switching section $S_1$, is connected to the input of a logarithmic amplifier LV, the output of which is connected to an image reconstruction device BI known per se. The generators $H_1$, $H_2$, $V_1$ and $V_2$ can be controlled individually via appropriate frequency multiplying units from a common clock signal source which produces a clock signal of e.g. 50 Hz. The signals produced by generators $H_2$ and $V_2$ may also be used as scan path controlling signals for the image reconstruction device BI, which is diagrammatically shown in the drawing by broken lines. Naturally, the command unit 13, in the operating mode for making a tomogram, is likewise operative to irradiate the object successively from various directions with the regrouping made at the beginning of said operating mode of the radiation source, slotted masks, object carrier and detector device.

Thus a tomographic system arranged in accordance with the invention makes it possible by making use of one and the same image intensifier and video camera tube connected therewith, to either produce an overall picture or a tomogram.

It is observed yet that the invention is not restricted to the above discussed organisation, wherein subsequent to the forming of an overall picture, with a stationary object, the radiation source, slotted masks and detector device with connected video camera, are regrouped as diagrammatically shown on the drawing by broken lines.

It is also possible for instance to design an arrangement wherein the assembly comprising the radiation source, capture screen, image intensifier with connected video camera tube, is rotatable about the radiation source, and further movable in vertical direction. When an overall picture has been formed with an arrangement as diagrammatically shown in the drawing by broken lines, said assembly in its entirety can be rotated relative to the axis extending vertically through the radiation source 1, over such angle that by means of a slotted mask, such as 3, positioned between the source and the object, the one outer ray of the beam extends through point 0 and the other outer ray is extending outside the object.

I claim:

1. A tomography system comprising a source for producing penetrating radiation, such as X-rays or gama-rays, a support arrangement for supporting an object, beam collimating means including a set of slotted masks serving to irradiate an object placed on said support arrangement with one or more diverging beams of radiation, a detector arrangement for converting radiation transmitted through and along the object into electric signals, and an image reconstruction device for processing electric signals, characterized in that the means for deflecting the scanning beam of a video camera which in an optical sense is being rigidly coupled with the output of the detector arrangement, are coupled to a selectively switchable electronic control device by means of which control device the format and/or resolution of the picture as being read out by the video camera can be adjusted to a selected value; a selectively adjustable positioning device being further provided for grouping spatially relative to one another and dependent on the operating mode selected for said electronic control device, the combination of radiation source, slotted masks and detector arrangement with respect to said support arrangement in such a manner that either an overall picture of an object placed on said support arrangement, or a tomographic image of one or more cross-sections of the object portion corresponding to said overall picture can be made.

2. A system according to claim 1, characterized in that said electronic control device comprises an operating mode switching device serving to select the manner in which the picture formed on the input screen of the video camera is scanned.

3. A system according to claim 2, characterized in that said operating mode switching device is coupled to a command unit serving to adjust said position device for a spatial configuration of the irradiation picture forming means corresponding to the selected operating mode.

4. A unit comprising a detector device and a video camera connected thereto, the deflection means and the output thereof being coupled to a selectively switchable, electronic control device which, depending upon the selected operating mode, determines the height and width of a scanned image and/or the resolution thereof, which unit forms part of a system according to claim 1.

* * * * *